(12) United States Patent
Choi

(10) Patent No.: US 9,066,886 B2
(45) Date of Patent: Jun. 30, 2015

(54) TRANSDERMAL DRUG DELIVERY SYSTEM CONTAINING GRANISETRON

(75) Inventor: Hoo-Kyun Choi, Gwangju (KR)

(73) Assignee: TAHO PHARMACEUTICALS, LTD., Taipei (TW)

( * ) Notice: Subject to any disclaimer, the term of this patent is extended or adjusted under 35 U.S.C. 154(b) by 355 days.

(21) Appl. No.: 12/811,003

(22) PCT Filed: Aug. 22, 2008

(86) PCT No.: PCT/KR2008/004900
§ 371 (c)(1),
(2), (4) Date: Jun. 28, 2010

(87) PCT Pub. No.: WO2009/088142
PCT Pub. Date: Jul. 16, 2009

(65) Prior Publication Data
US 2010/0285133 A1    Nov. 11, 2010

(30) Foreign Application Priority Data

Jan. 9, 2008    (KR) .................. 10-2008-0002388

(51) Int. Cl.
*A61K 9/00*    (2006.01)
*A61P 1/08*    (2006.01)
*A61K 9/70*    (2006.01)

(52) U.S. Cl.
CPC .................................. *A61K 9/7061* (2013.01)

(58) Field of Classification Search
CPC ..... A61K 9/7061; A61K 31/439; A61K 9/00; A61P 1/08
See application file for complete search history.

(56) References Cited

U.S. PATENT DOCUMENTS

| | | | | |
|---|---|---|---|---|
| 5,858,340 | A | * | 1/1999 | Briggs et al. ............... 424/70.19 |
| 6,309,663 | B1 | * | 10/2001 | Patel et al. ..................... 424/450 |
| 2005/0260255 | A1 | * | 11/2005 | Terahara et al. .............. 424/449 |
| 2006/0078604 | A1 | * | 4/2006 | Kanios et al. ................. 424/449 |
| 2006/0177493 | A1 | * | 8/2006 | Altenschopfer et al. ...... 424/449 |

FOREIGN PATENT DOCUMENTS

| | | |
|---|---|---|
| KR | 10-2005-0116365 A | 12/2005 |
| KR | 10-2006-0049598 A | 5/2006 |
| WO | 1998/53815 A1 | 12/1998 |
| WO | 03/013482 A1 | 2/2003 |
| WO | WO 03/013482 * | 2/2003 |
| WO | WO 04/000263 * | 12/2003 |
| WO | 2004/069141 A2 | 8/2004 |
| WO | 2006/028863 A1 | 3/2006 |
| WO | 2006/124807 A1 | 11/2006 |
| WO | WO 2006124807 A1 * | 11/2006 |

\* cited by examiner

*Primary Examiner* — Ernst V Arnold
(74) *Attorney, Agent, or Firm* — Lucas & Mercanti, LLP

(57) ABSTRACT

Disclosed herein is a transdermal system in a matrix form capable of enhancing granisetron carrying efficiency and improving transdermal absorption while inhibiting recrystallization, which comprises: at least one transdermal enhancer selected from a group consisting of polyglyceryl-3 oleate, polyethyleneglycol-20 almond glyceride, polyethyleneglycol-12 palm kernel glyceride, isopropyl myristate and oleyl alcohol; and an acrylate polymer.

5 Claims, No Drawings

TRANSDERMAL DRUG DELIVERY SYSTEM CONTAINING GRANISETRON

CROSS-REFERENCE TO RELATED APPLICATIONS

This application is a 371 of PCT/KR2008/004900 filed on Aug. 22, 2008, which claims the benefit of Korean Patent Application No. 10-2008-0002388 filed on Jan. 9, 2008, the contents of each of which are incorporated herein by reference.

TECHNICAL FIELD

The present invention relates to a transdermal system containing granisetron and, more particularly, a transdermal composition containing granisetron applicable to a continuous transdermal drug delivery system.

Nausea and vomiting are symptoms commonly occurring in cancer patients, which may be caused by side effects of anticancer agents administered to the patients. Such symptoms generally cause a cancer patient to suffer from depression and may lead to anorexia and/or poor appetite, resulting in weight loss. Accordingly, these conditions may cause weakness in the cancer patient and ultimately decrease resistance to the cancer of the patient, thus reducing therapeutic effect. Therefore, if an antiemetic agent is additionally provided when an anticancer agent that may induce vomiting is administered to a cancer patient, side effects of nausea and vomiting may be minimized.

As a drug for inhibiting nausea and vomiting, granisetron is an antagonist of $5-HT_3$ (5-hydroxytryptamine3) receptors and is well known to inhibit vomiting caused by side effects of anticancer agents when the drug is administered to a patient undergoing chemotherapy.

Granisetron is generally administered by intravenous injection (IV) or oral administration, however, IV administration may induce a decrease in patient compliance due to inconvenience caused by repeated use and avoidance of the injection and, in addition, may cause bacterial infection unless drug formulations are carefully managed. On the other hand, the oral administration requires frequent dosing and may have problems in administration to patients suffering from severe nausea and vomiting. Accordingly, applying granisetron to a transdermal drug delivery system may solve problems in drug administrations via oral route, IV, etc. while constantly maintaining blood drug concentrations.

A transdermal drug delivery method may be generally classified into an active process using, for example, electric energy and a passive process through passive drug transportation without the energy. The active process exhibits excellent effects but requires substantial energy consumption and complicated construction for drug delivery to a patient. The passive process may also be divided into a reservoir type system and a matrix type system. The reservoir type system carries drug on a gel carrier and is advantageous in that a high concentration of a drug may be carried and a drug permeation rate (or flux) may be controlled through a drug flux control membrane. However, a process for production of the reservoir type system is relatively complicated and the reservoir type system is thicker than the matrix type system, therefore, when the reservoir type system is applied to a patient's skin, patient compliance may be reduced in view of cosmetic features. On the contrary, the matrix type system directly dissolves or disperses a drug in a polymer adhesive, thus being fabricated by a simple process. Additionally, the matrix type system may be a thinner and more flexible formulation than the reservoir type system, thereby enhancing patient compliance.

BACKGROUND ART

The present invention discloses a transdermal system in a matrix form, comprising an active ingredient dissolved or dispersed in a polymer, wherein the active ingredient contains granisetron.

Conventional techniques regarding transdermal drug delivery systems containing granisetron have recently been described, which include, for example, Korean Patent Laid-Open Publication No. 10-2005-0116365 disclosing a transdermal system consisting of granisetron and an acrylic adhesive. This document describes that the transdermal system must have an area of 40 $cm^2$ in order to reach a concentration identical to $C_{max}$ (3.6 ng/ml), which is obtained by administering a tablet with 1 mg of granisetron. However, if the area of the transdermal system is enlarged, patient compliance may be decreased. For this reason, the transdermal system preferably has a reduced size.

WO-03013482 discloses a transdermal system of a $5-HT_3$ antagonist, comprising an adhesive dressing that includes a copolymer simultaneously having a hard segment and a soft segment, a plasticizer and a drug. However, if a transdermal formulation is prepared by the technique in this document, a synthesis process to prepare the copolymer may be added, leading to a very complicated process for fabrication of the transdermal system.

WO 2006/028863 discloses a transdermal system of an antiemetic agent and a process for fabrication thereof. This technique is characterized in that a transdermal absorption enhancer selected from a group consisting of: N-methyl-2-pyrrolidone; polyvinylpyrrolidone; polyethylenegygol 400; laureth-4; mineral oil; and sorbitan monolaurate, which is used alone or in combination of two or more thereof, may be mixed with an adhesive to prepare a matrix type formulation. Although this document suggests a variety of transdermal absorption enhancers capable of being mixed with an acrylic adhesive having a hydroxyl functional group, if a content of the enhancer exceeds 5% of a solid content of the adhesive, the enhancer may decrease cohesive strength of the adhesive. As a result, the transdermal system attached to skin may exhibit a cold flow phenomenon. In addition, mineral oil may not be sufficiently combined with other ingredients in the system. Moreover, the transdermal system has a problem in that a drug contained in the transdermal system may crystallize during storage unless a crystallization inhibitor such as polyvinyl pyrrolidone is added.

DISCLOSURE OF INVENTION

Technical Problem

Accordingly, as a result of extensive studies and investigation into approaches to enhance granisetron carrying efficiency in a matrix of a transdermal system, to inhibit recrystallization and to improve transdermal absorption, the present inventors provided a novel transdermal system in a matrix form capable of enhancing granisetron carrying efficiency and improving transdermal absorption while inhibiting recrystallization, which comprises: an adhesive consisting of an acrylate polymer with a hydroxyl group and another acrylate polymer without any functional group in a ratio of 20 to 99:1 to 80; and at least one transdermal enhancer selected from a group consisting of polyglyceryl-3 oleate, polyethyleneglycol-20 (PEG-20) almond glyceride, polyethyleneglycol-12 (PEG-12) palm kernel glyceride, isopropyl myristate and oleyl alcohol, in the matrix.

Technical Solution

Therefore, an object of the present invention is to provide a transdermal system containing granisetron as an active ingredient, which is a 5-HT$_3$ antagonist with excellent effects for inhibiting nausea and vomiting, so as to enhance granisetron carrying efficiency, inhibit recrystallization and improve transdermal absorption while having a simple construction.

Details of the above object and other features of the present invention will be more clearly understood from the following detailed description.

An amount of granisetron used as an active ingredient may range from 1 to 6% by weight ("wt. %") of the total weight of a matrix layer except a backing membrane and a release liner and, preferably from 3 to 5 wt. %. If the amount exceeds 6 wt. %, some of the drug in the transdermal system may crystallize, inhibiting transdermal permeation.

The present invention may use a transdermal enhancer for the purpose of improving transdermal absorption of granisetron and solubility of the drug in the transdermal system during storage thereof. Such a transdermal enhancer may include at least one selected from a group consisting of polyglyceryl-3 oleate, PEG-20 almond glyceride, PEG-12 palm kernel glyceride, isopropyl myristate and oleyl alcohol. An amount of the transdermal enhancer used herein may range from 0.1 to 25 wt. % of the total weight of the matrix layer except the backing membrane and the release liner and, preferably from 2 to 15 wt. %. If the amount is less than 0.1 wt. %, the transdermal permeation is little improved. On the other hand, when the amount exceeds 25 wt. %, cohesive strength of the transdermal system is reduced and cold flow may occur when the transdermal system is applied to affected parts, leading to a decrease in patient compliance.

The adhesive for skin attachment of the transdermal system and for functioning as a carrier for ingredients of the system may include a combined adhesive including an acrylate polymer with a hydroxyl group and another acrylate polymer without any functional group.

Preferred examples of the acrylate polymer having a hydroxyl group used herein may include Durotak 87-2287 (acrylate-vinylacetate), Durotak 87-2510 (acrylate), Durotak 87-2516 (acrylate-vinylacetate), Durotak 87-2525 (acrylate-vinylacetate), Durotak 87-4287 (acrylate-vinylacetate), and so forth. Preferred examples of the acrylate polymer without any functional group used herein may include Durotak 87-900A (acrylate), Durotak 87-9301 (acrylate), Durotak 87-4098 (acrylate-vinylacetate), and so forth.

The acrylate polymer having a hydroxyl group exhibits excellent transdermal drug permeation but lacks cohesive strength, causing cold flow when the transdermal system is applied to an affected part. The acrylate polymer without any functional group has favorable cohesive strength but relatively low transdermal drug permeation compared to the acrylate polymer having a hydroxyl group. Therefore, both the polymers may be mixed together to prepare a combined adhesive so as to achieve synergistic effects. The combined adhesive may include 20 to 99 wt. %, preferably 50 to 95 wt. % of the acrylate polymer having a hydroxyl group. If the amount of the acrylate polymer having a hydroxyl group is less than 20 wt. %, transdermal drug permeation effects are not observed. When the amount exceeds 99 wt. %, the transdermal system may have reduced adhesiveness and cohesive strength, causing cold flow when the transdermal system is applied to an affected part and leading to a decrease in patient compliance.

The backing membrane may include a polymer film commercially available in the art, which is used for transdermal systems, is non-permeable to active ingredients and includes, for example, polyester, polypropylene, polyethylene, polyurethane, ethylene vinyl acetate copolymers and the like.

The release liner may include a polymer film commercially available in the art, which must not remain a matrix adhesive of the transdermal system but be easily released from the same, when the transdermal system is applied to an affected part.

Best Mode

Hereinafter, preferred embodiments and examples of the present invention will be described in detail. However, these examples are given for the purpose of illustration and are not intended to limit the invention.

EXAMPLE 1

After 30 mg of granisetron was dissolved in 180 mg of ethanol, 520 mg of an adhesive containing an acrylate polymer with a hydroxyl group (manufactured by National Starch & Chemical Co., Durotak 87-2516) and 130 mg of another adhesive containing an acrylate polymer without any functional group (manufactured by National Starch & Chemical Co., Durotak 87-9301) were added to the granisetron solution. Subsequently, 60 mg of oleyl alcohol and 12 mg of polyglyceryl-3 oleate (manufactured by Gattefosse, Plurol Oleique) were added to the mixture under homogeneous stirring. The obtained solution was applied to a silicone coated release liner (manufactured by 3M Company, 1362) up to a dry thickness of 150 µm, dried at room temperature for 2 hours, and then, at 80° C. for 10 minutes. The resultant acrylic adhesive layer was transferred to a polyester film (manufactured by 3M Company) as a backing membrane by pressing the adhesive layer to the film. Finally, the transferred film was cut into 16 cm$^2$-sized pieces, which were obtained as a final product.

EXAMPLE 2

After 30 mg of granisetron was dissolved in 180 mg of ethanol, 520 mg of an adhesive containing an acrylate polymer with a hydroxyl group (manufactured by National Starch & Chemical Co., Durotak 87-2516) and 130 mg of another adhesive containing an acrylate polymer without any functional group (manufactured by National Starch & Chemical Co., Durotak 87-9301) were added to the granisetron solution. Subsequently, 15 mg of polyethyleneglycol-12 palm kernel glyceride was added to the mixture under homogeneous stirring. The obtained solution was applied to a silicone coated release liner (manufactured by 3M Company, 1362) up to a dry thickness of 150 µm, dried at room temperature for 2 hours, and then, at 80° C. for 10 minutes. The resultant acrylic adhesive layer was transferred to a polyester film (manufactured by 3M Company, Scotch pack 9732) as a backing membrane by pressing the adhesive layer to the film. Finally, the transferred film was cut into 16 cm$^2$-sized pieces, which were obtained as a final product.

EXAMPLE 3

A patch type product was produced by the same procedure as in Example 2, except that polyglyceryl-3 oleate was used in place of polyethyleneglycol-12 palm kernel glyceride.

EXAMPLE 4

A patch type product was produced by the same procedure as in Example 2, except that polyethyleneglycol-20 almond glyceride was used in place of polyethyleneglycol-12 palm kernel glyceride.

EXAMPLE 5

A patch type product was produced by the same procedure as in Example 2, except that a mixture comprising 15 mg of polyglyceryl-3 oleate and 15 mg of polyethyleneglycol-12 palm kernel glyceride in a ratio of 1:1 was used in place of polyethyleneglycol-12 palm kernel glyceride.

EXAMPLE 6

A patch type product was produced by the same procedure as in Example 2, except that 30 mg of polyglyceryl-3 oleate was used in place of polyethyleneglycol-12 palm kernel glyceride.

EXAMPLE 7

A patch type product was produced by the same procedure as in Example 2, except that 60 mg of oleyl alcohol was used in place of polyethyleneglycol-12 palm kernel glyceride.

EXAMPLE 8

A patch type product was produced by the same procedure as in Example 2, except that 60 mg of isopropyl myristate was used in place of polyethyleneglycol-12 palm kernel glyceride.

EXAMPLE 9

A patch type product was produced by the same procedure as in Example 2, except that a mixture comprising 60 mg of oleyl alcohol and 3 mg of polyglyceryl-3 oleate was used in place of polyethyleneglycol-12 palm kernel glyceride.

EXAMPLE 10

A patch type product was produced by the same procedure as in Example 2, except that a mixture comprising 60 mg of oleyl alcohol and 6 mg of polyglyceryl-3 oleate was used in place of polyethyleneglycol-12 palm kernel glyceride.

EXAMPLE 11

A patch type product was produced by the same procedure as in Example 2, except that a mixture comprising 60 mg of oleyl alcohol and 9 mg of polyglyceryl-3 oleate was used in place of polyethyleneglycol-12 palm kernel glyceride.

EXAMPLE 12

A patch type product was produced by the same procedure as in Example 2, except that a mixture comprising 315 mg of Durotak 87-2516 and 315 mg of Durotak 87-9301 was used in place of Durotak 87-2516 and Durotak 87-9301 in a ratio of 4:1.

EXAMPLE 13

A patch type product was produced by the same procedure as in Example 1, except that 30 mg of oleyl alcohol and 12 mg of polyglyceryl-3 oleate (manufactured by Gattefosse, Plurol Oleique) were used in place of 60 mg of oleyl alcohol and 12 mg of polyglyceryl-3 oleate (manufactured by Gattefosse, Plurol Oleique).

EXAMPLE 14

A patch type product was produced by the same procedure as in Example 1, except that 45 mg of oleyl alcohol and 12 mg of polyglyceryl-3 oleate (manufactured by Gattefosse, Plurol Oleique) were used in place of 60 mg of oleyl alcohol and 12 mg of polyglyceryl-3 oleate (manufactured by Gattefosse, Plurol Oleique).

COMPARATIVE EXAMPLE 1

After 10 mg of granisetron was dissolved in 60 mg of ethanol, 210 mg of an acrylate polymer without any functional group (manufactured by National Starch & Chemical Co., Durotak 87-9301) was added to the granisetron solution. The mixture was applied to a silicone coated release liner up to a dry thickness of 150 μm, dried at room temperature for 2 hours, and then, at 80° C. for 10 minutes. The resultant acrylic adhesive layer was transferred to a polyester film (manufactured by 3M Company) as a backing membrane by pressing the adhesive layer to the film. Finally, the transferred film was cut into 16 cm$^2$-sized pieces, which were obtained as a final product.

COMPARATIVE EXAMPLE 2

A patch type product was produced by the same procedure as in Comparative Example 1, except that an acrylate polymer without any functional group, Durotak 87-4098, was used in place of the acrylate polymer without any functional group (manufactured by National Starch & Chemical Co., Durotak 87-9301).

COMPARATIVE EXAMPLE 3

A patch type product was produced by the same procedure as in Comparative Example 1, except that an acrylate polymer without any functional group, Durotak 87-900A, was used in place of the acrylate polymer without any functional group (manufactured by National Starch & Chemical Co., Durotak 87-9301).

COMPARATIVE EXAMPLE 4

A patch type product was produced by the same procedure as in Comparative Example 1, except that an acrylate polymer having a carboxyl group as well as a hydroxyl group, Durotak 87-2074, was used in place of the acrylate polymer without any functional group (manufactured by National Starch & Chemical Co., Durotak 87-9301).

COMPARATIVE EXAMPLE 5

A patch type product was produced by the same procedure as in Comparative Example 1, except that an acrylate polymer having a carboxyl group, Durotak 87-2100, was used in place of the acrylate polymer without any functional group (manufactured by National Starch & Chemical Co., Durotak 87-9301).

COMPARATIVE EXAMPLE 6

A patch type product was produced by the same procedure as in Comparative Example 1, except that an acrylate polymer having a carboxyl group, Durotak 87-2677, was used in place of the acrylate polymer without any functional group (manufactured by National Starch & Chemical Co., Durotak 87-9301).

COMPARATIVE EXAMPLE 7

A patch type product was produced by the same procedure as in Comparative Example 3, except that 5 mg of sorbitan monooleate was added.

COMPARATIVE EXAMPLE 8

A patch type product was produced by the same procedure as in Comparative Example 1, except that 10 mg of polyethyleneglycol-20 almond glyceride was added and an adhesive solution containing an acrylate polymer having a hydroxyl group (manufactured by National Starch & Chemical Co., Durotak 87-2516) was used in place of the acrylate polymer without any functional group (manufactured by National Starch & Chemical Co., Durotak 87-9301).

COMPARATIVE EXAMPLE 9

A patch type product was produced by the same procedure as in Comparative Example 1, except that 10 mg of polyethyleneglycol-12 palm kernel glyceride was added and an adhesive solution containing an acrylate polymer having a hydroxyl group (manufactured by National Starch & Chemical Co., Durotak 87-2516) was used in place of the acrylate polymer without any functional group (manufactured by National Starch & Chemical Co., Durotak 87-9301).

COMPARATIVE EXAMPLE 10

A patch type product was produced by the same procedure as in Comparative Example 1, except that 10 mg of polyethyleneglycol-8 glyceryl linoleate was added and an adhesive solution containing an acrylate polymer having a hydroxyl group (manufactured by National Starch & Chemical Co., Durotak 87-2516) was used in place of the acrylate polymer without any functional group (manufactured by National Starch & Chemical Co., Durotak 87-9301).

COMPARATIVE EXAMPLE 11

A patch type product was produced by the same procedure as in Comparative Example 1, except that 10 mg of oleyl alcohol was added and an adhesive solution containing an acrylate polymer having a hydroxyl group (manufactured by National Starch & Chemical Co., Durotak 87-2516) was used in place of the acrylate polymer without any functional group (manufactured by National Starch & Chemical Co., Durotak 87-9301).

EXPERIMENTAL EXAMPLE

Each product, that is, each transdermal system, obtained by the above examples and comparative examples was applied to a hairless mouse's skin to determine transdermal permeation effects thereof. Immediately before experimentation, the hairless mouse skin was excised. The product to be tested was cut into a round piece having an area of 2 cm$^2$, followed by attaching the cut piece to the excised skin. Fixing the treated skin to a flow-through diffusion cell using a clamp, several samples were collected at intervals of 4 hours over a period of 28 hours. The collected samples were subjected to quantification via high-performance liquid chromatography (HPLC). The measured values were used to calculate a drug permeation rate and the results are shown in Table 1. An isotonic phosphate buffer (pH 7.4) was placed in a receptor cell, maintained at 37° C., while homogeneously agitating the buffer solution using a magnetic stirrer. Analysis conditions are as follows:

<Analysis Conditions>
Column: Luna C8 (4.6×150 mm)
Mobile phase: 25 mM acetate buffer/acetonitrile (68/32)
Detector: UV 301 nm
Flow rate: 1 ml/min

TABLE 1

| | Transdermal absorption rate ($\mu g/cm^2/hr$) |
|---|---|
| Example 1 | 15.01 |
| Example 2 | 10.93 |
| Example 3 | 11.68 |
| Example 4 | 10.61 |
| Example 5 | 13.21 |
| Example 6 | 12.34 |
| Example 7 | 13.19 |
| Example 8 | 11.65 |
| Example 9 | 11.04 |
| Example 10 | 12.77 |
| Example 11 | 12.11 |
| Example 12 | 13.79 |
| Example 13 | 12.84 |
| Example 14 | 13.77 |
| Comparative Example 1 | 2.90 |
| Comparative Example 2 | 2.73 |
| Comparative Example 3 | 3.90 |
| Comparative Example 4 | 0.03 |
| Comparative Example 5 | 1.41 |
| Comparative Example 6 | 0.51 |
| Comparative Example 7 | 4.70 |
| Comparative Example 8 | 10.49 |
| Comparative Example 9 | 9.94 |
| Comparative Example 10 | 10.47 |
| Comparative Example 11 | 10.59 |

As shown in the Table 1, it was found that each product prepared in Examples 1 to 14 had a high drug permeation rate (that is, transdermal absorption rate) of not less than 10 $\mu g/cm^2/hr$, while each of the controls prepared in Comparative Example 1 to 7 exhibited a relatively low drug permeation rate of 5 $\mu g/cm^2/hr$ or less. Theses results identified excellent performance of the present invention. The products prepared in Comparative Examples 8 to 11 also exhibited relatively high transdermal absorption rates, however, when each of the products was attached to a portion of skin for 24 hours, followed by observing the portion of skin, it was found that cold flow occurred on the product due to reduced cohesive strength and an adhesive contained in the product was partially leaked out of the backing membrane and stained surroundings.

Industrial Applicability

According to the present invention, there is provided a transdermal granisetron delivery system for inhibiting nausea and vomiting which can be administered to a patient undergoing chemotherapy.

The transdermal granisetron delivery system of the present invention can enhance granisetron carrying efficiency and improve transdermal absorption while inhibiting recrystallization and is advantageous in that it can continuously deliver a drug via a transdermal path so as to effectively inhibit nausea and vomiting, which may be side effects of anticancer agents administered to a cancer patient, thereby reducing inconvenience and improving compliance of the patient.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A transdermal granisetron delivery system in a matrix form comprising:
   granisetron as an active ingredient and
   a matrix, including:
      an adhesive consisting of an acrylate polymer with a hydroxyl group and another acrylate polymer without any functional group in a ratio of 50 to 95:5 to 50; and
      at least one transdermal enhancer selected from a group consisting of polyglyceryl-3 oleate, polyethyleneglycol-20 (PEG-20) almond glyceride, polyethyleneglycol-12 (PEG-12) palm kernel glyceride, isopropyl myristate and oleyl alcohol,
   wherein
   granisetron is contained in an amount of 1 to 6 wt. % of the total weight of the matrix except a backing membrane and a release liner of the transdermal system;
   the transdermal enhancer is contained in an amount of 0.1 to 25 wt. % of the total weight of the matrix except a backing membrane and a release liner of the transdermal system and
   the transdermal granisetron delivery system has a drug permeation rate of not less than 10 μg/cm$^2$/hr as measured on a hairless mouse's skin.

2. The transdermal granisteron delivery system according to claim 1, wherein the backing membrane includes at least one selected from the group consisting of polyester, polypropylene, polyethylene, ethylene vinyl acetate and polyurethane.

3. A transdermal granisetron delivery system in a matrix form comprising:
   granisetron as an active ingredient; and,
   a matrix, including:
      an adhesive consisting of an acrylate polymer with a hydroxyl group and another acrylate polymer without any functional group in a ratio of 4:1 to 1:1; and
      at least one transdermal enhancer selected from a group consisting of polyglyceryl-3 oleate, polyethyleneglycol-20 (PEG-20) almond glyceride, polyethyleneglycol-12 (PEG-12) palm kernel glyceride, isopropyl myristate and oleyl alcohol,
   wherein
   granisetron is contained in an amount of 1 to 6 wt. % of the total weight of the matrix except a backing membrane and a release liner of the transdermal system;
   the transdermal enhancer is contained in an amount of 0.1 to 25 wt. % of the total weight of the matrix except a backing membrane and a release liner of the transdermal system and
   the transdermal granisetron delivery system has a drug permeation rate of not less than 10 μg/cm$^2$/hr as measured on a hairless mouse's skin.

4. The transdermal granisetron delivery system according to claim 3, wherein the adhesive consists of an acrylate polymer with a hydroxyl group and another acrylate polymer without any functional group in a ratio of 4:1.

5. The transdermal granisetron delivery system according to claim 3, wherein the adhesive consists of an acrylate acrylate polymer with a hydroxyl group and another acrylate polymer without any functional group in a ratio of 1:1.

* * * * *